(12) United States Patent
Doemling et al.

(10) Patent No.: US 6,355,726 B1
(45) Date of Patent: Mar. 12, 2002

(54) METHOD FOR PRODUCING POLYMERS HAVING NUCLEO-BASES AS SIDE-GROUPS

(75) Inventors: Alexander Doemling; Wolfgang Richter, both of Munich (DE)

(73) Assignee: Morphochem AG, Martinsried (DE)

( * ) Notice: Subject to any disclaimer, the term of this patent is extended or adjusted under 35 U.S.C. 154(b) by 0 days.

(21) Appl. No.: 09/423,594

(22) PCT Filed: May 14, 1998

(86) PCT No.: PCT/EP98/02860

§ 371 Date: Nov. 10, 1999

§ 102(e) Date: Nov. 10, 1999

(87) PCT Pub. No.: WO98/51697

PCT Pub. Date: Nov. 19, 1998

(30) Foreign Application Priority Data

May 14, 1997 (DE) .......................... 197 20 165
May 14, 1997 (DE) .......................... 197 20 216

(51) Int. Cl.$^7$ .................. C07H 21/00; C07K 1/04; C07K 14/00; C07D 473/00; C07D 239/24
(52) U.S. Cl. .................. 525/54.1; 525/54.2; 525/54.3; 530/812; 530/815; 436/8; 436/528; 436/531; 436/532

(58) Field of Search ................. 525/54.1, 54.2, 525/54.3; 530/812, 815; 436/528, 531, 532, 535, 8

(56) References Cited

U.S. PATENT DOCUMENTS 5,770,455 A * 6/1998 Cargill et al. ................ 436/518
5,874,553 A * 2/1999 Peyman et al. ............. 536/22.1

FOREIGN PATENT DOCUMENTS

WO  WO 96/15143  * 5/1996

* cited by examiner

Primary Examiner—Nathan M. Nutter
(74) Attorney, Agent, or Firm—Frommer Lawrence & Haug LLP

(57) ABSTRACT

A process for the preparation of polymers having nucleo-bases as side groups by means of multicomponent reactions, especially the Ugi reaction, is described. Because of the multicomponent nature of preparation, the properties of the polymers can be varied substantially better than has hitherto been possible and can be adapted to requirements for use as an antisense or antigen therapeutic agent or as a diagnostic agent.

10 Claims, No Drawings

METHOD FOR PRODUCING POLYMERS HAVING NUCLEO-BASES AS SIDE-GROUPS

The invention relates to a process for the preparation of polymers having nucleobases as side groups by means of multicomponent reactions, especially the Ugi reaction.

The present invention relates also to multifunctional isonitriles, to a process for their preparation and to their use in multicomponent reactions. Such isonitriles can be used in the process according to the invention for the preparation of polymers having nucleobases as side groups.

Multicomponent reactions (MCRs) are valuable processes in organic synthesis. They are used, for example, in synthesising antibiotics, peptides, etc., that is to say complex molecules having a high degree of diversity. In the case of customary MCRs, such as, for example, a four-component reaction (4-CC), an isonitrile, an aldehyde, a carboxylic acid and an amine are reacted to form a defined product. The isonitriles used hitherto have been monofunctional compounds, with the result that the variety of products of such multicomponent reactions has been limited (see Isonitrile Chemistry; I. Ugi (Ed.), Academic Press, New York, London 1971) and the reaction in question has been complete as soon as the individual components have finished reacting with one another.

Regulatory action on gene expression by means of polymeric peptide nucleic acids (PNA) was first described in the sixties by Svachkin et al. (R. A. Paégle, M. G. Plata, M. Yu. Lidak, S. A. Giller, Yu. P. Shvachkin, in: Present State of the Chemotherapy of Malignant Tumors [in Russian], Riga (1968), 103 ff.; Review: Yu. P. Shavachkin, G. P. Mishin, G. A. Korshunova, Russian Chemical Reviews, 51, 1982, 178–188). In 1978 Zamecnik and Stephenson introduced the terms "antisense" and "antigen": those terms describe mechanisms by which it is possible to intervene therapeutically in the translation and transcription of genes (Proc. Natl. Acad. Sci. U.S.A., 1978, 75, 280 and 285).

In the antisense strategy, an antisense molecule binds to mRNA and thus prevents its translation to a protein. In the antigen strategy, a triple helix of the antigen molecule with the double-stranded DNA is formed, thus modifying transcription into mRNA (E. Uhlmann, A. Peyman, Chem. Rev., 90, 1990, 544–584). In this context, various substances are potential therapeutic agents for the treatment of viral diseases, cancer, etc., in various clinical phases.

A good antisense molecule should inter alia satisfy the following requirements:

1. It should have good accessibility to the cell and cell nucleus without the assistance of so-called transfection reagents or liposomes;
2. It should have nuclease and peptidase resistance in order to obtain sufficient bioavailability; and
3. It should recognise precisely the sequence of the natural sense strand.

The PNA described by Nielsen et al. (Science 1991, 254, 1497–1500; WO 92/20702) has proved to be a highly promising antisense and antigen polymer, and has also been used in a variety of ways as a tool in molecular biology. This is attributable primarily to the high affinity of the PNA for the sense strand (DNA, RNA) combined with very good sequence specificity. PNA is able to identify mismatches in sequences substantially better than do natural DNA and RNA. Moreover, pyrimidine-rich PNA strands are able to wind up the DNA double helix and form a $(PNA)_2DNA$ triple helix. Such structures are potential translation and replication complex mimetics and it might be possible to use them to turn specific genes on and off. Various properties of PNA still need to be improved and optimised for in vivo use, however. For example, PNA does not have cell-accessibility. The $(PNA)_2DNA$ triple helix formation mentioned occurs only in the case of pyrimidine-fich PNA strands and only at non-physiological salt concentrations. PNAs aggregate and have poor solubility in water. PNA—itself a polar polymer—binds to the DNA or RNA target structure in both parallel and anti-parallel manner with similar binding constants. There have also been reports of PNA having strong cytotoxic effects (EP 0 672 677 A2).

As has been shown, new improved PNAs are found most effectively by screening a large number of variants (S. Jordan et al., Bioorganic & Medicinal Chemistry Letters, 1997, 7, 681 and 687). The methods of PNA synthesis described hitherto, which are based on sequential two-component reactions of monomers which themselves must be synthesised from suitable commercial precursors via many steps, do not appear to be optimally suited to the systematic and rapid production of a large number of analogues (M. Egholm et al., Journal of the American Chemical Society, (1992) 114, 1895).

The problem underlying the present invention is accordingly to provide a process by which complex monomers, oligomers and polymers having nucleobases as side groups, and especially PNAs having a large capacity for variation, can be produced.

A further problem of the present invention is to provide a component with which the diversity of MCRs and especially of processes for the preparation of polymers having nucleobases as side groups can be considerably increased and complex molecules can be synthesised, that is to say a component that can be reacted in an MCR-type reaction. Such components must satisfy the following preconditions:

1. They must be easy and inexpensive to produce;
2. The protecting groups used therein must be readily removable, that is to say under mild conditions;
3. The protecting groups used therein must be stable under customary reaction conditions for the reaction of other functional groups;
4. The components must be so synthesised that, after the removal of a protecting group, functional groups suitable for an MCR are freed without other groups, for example functional groups of the components or of the reactants, being modified.

According to the invention, there is disclosed a process for the preparation of compounds of formula (I)

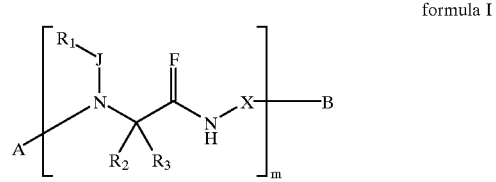

formula I characterised in that compounds of formulae

II

III

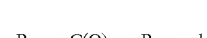

IV

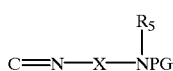

(V)

are reacted with one another, optionally simultaneously, in a first step,
as appropriate one or more protecting groups are removed, and the reaction is repeated m times,
wherein, after the first step, the product of each preceding step is used instead of the compound of formula II,
wherein
- m is 0 or an integer from 1 to 1000, preferably from 1 to 300, more especially from 1 to 100, especially from 1 to 50, from 1 to 30, from 1 to 10 or from 1 to 5,
- A is a radical of the amino component being a radical customary in the Ugi reaction, such as a hydrogen atom, a substituent, (cyclo)alkyl, (cyclo)alkenyl, (cyclo)alkynyl, aroyl, heteroaroyl, a heterocycle, a fluorescent label, an intercalator, an antibiotic, a minor groove binder, a major groove binder, a biotinyl radical, an intercalating radical, an alkylating radical, a steroid, a lipid, a polyamine, an agent that facilitates cell uptake, a saccharide or oligosaccharide, an antisense polymer, a peptide, an antibody conjugate, a synthetic polymer or an appropriately modified surface,
- B is a hydrogen atom, a substituent, (cyclo)alkyl, (cyclo)alkenyl, (cyclo)alkynyl, aroyl, heteroaroyl, a heterocycle, a fluorescent label, an intercalator, an antibiotic, a minor groove binder, a major groove binder, a biotinyl radical, an intercalating radical, an alkylating radical, a steroid, a lipid, a polyamine, an agent that facilitates cell uptake, a saccharide or oligosaccharide, an antisense polymer, a peptide, an antibody conjugate, a synthetic polymer or an appropriately modified surface, or a radical X—NPG of compound V,
- $R_1$-G is selected from structures of the following formulae:

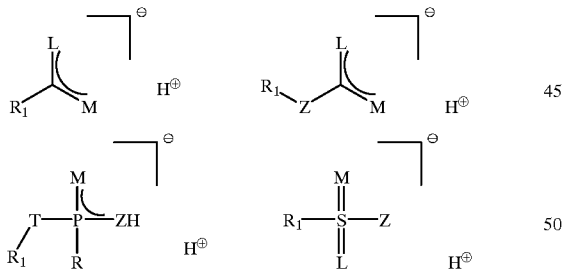

wherein the group $R_1$-G can be linked to the compound of formula IV by way of a molecular spacer via $R_1$ or R or $R_4$;
- $R_1$ and R each independently of the other is a radical of the acid component being a radical customary in the Ugi reaction, such as H, a substituent, (cyclo)alkyl, (cyclo)alkenyl, (cyclo)alkynyl, aroyl, heteroaroyl, a heterocycle, a fluorescent label, an intercalator, an antibiotic, a minor groove binder, a major groove binder, a biotinyl radical, an intercalating radical, an alkylating radical, a steroid, a lipid, a polyamine, a saccharide or oligosaccharide, an antisense polymer, a peptide, an antibody conjugate, a synthetic polymer or an appropriately modified surface, or a radical derived from the natural nucleobases or from synthetic nucleobases;
- L, M, T and Z each independently of the others represents O, S or $NR_4$, wherein $R_4$ represents H, fluorine, (cyclo)alkyl, (cyclo)alkenyl, (cyclo)alkynyl, aroyl, heteroaroyl, heterocycle, or —O(cyclo)alkyl, —Oaroyl, —S(cyclo)alkyl, —Saroyl;
- $R_2$ and $R_3$ each independently of the other represents a radical of the oxo component being a radical customary in the Ugi reaction, such as H, a substituent, (cyclo)alkyl, (cyclo)alkenyl, (cyclo)alkynyl, aroyl, heteroaroyl, a heterocycle, a fluorescent label, an intercalator, an antibiotic, a minor groove binder, a major groove binder, a biotinyl radical, an intercalating radical, an alkylating radical, a steroid, a lipid, a polyamine, a saccharide or oligosaccharide linked by way of an amine spacer, an antisense molecule, a peptide, an antibody conjugate, a synthetic polymer, a modified surface or a branching point P, which is in turn the starting point for a further DNA, RNA, PNA or peptide strand or for another oligomer or polymer,
- X has the following structure:

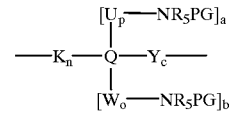

(VI)

each PG independently of any others represents an optionally orthogonal protecting group such as an amine-protecting group from the class of N-acyl derivatives, N-sulphonyl derivatives, N-alkyl derivatives, N-silyl derivatives, carbamates or salts thereof;
each of the radicals $R_5$ independently of any others represents a hydrogen atom, an unsubstituted or substituted alkyl, cycloalkyl, alkoxyalkyl or aryl group or a heterocycle;
the radicals U, W, K and Y each independently of the others represents an unsubstituted or substituted alkyl, alkenyl, alkynyl, alkanoyl, alkoxyalkanoyl, cycloalkyl or aryl group, an unsubstituted or substituted heterocycle or the group $NR_5$, wherein $R_5$ is as defined above;
a, b, c, n, o, and p each independently of the others is an integer from 0 to 10, preferably from 0 to 5;
Q is an unsubstituted or substituted alkyl, aryl, alkenyl, alkynyl, mono- or poly-valent alkanoyl, cycloalkyl, alkoxyalkanoyl, cycloalkanoyl or aroyl group or an unsubstituted or substituted heterocycle, or one of the groups $NR_5$, P, P(O), P(S), B, $BR_5$ and $SO_2$, wherein $R_5$ is as defined above and each of the indices a, b, o and p has a corresponding value;
F is an oxo, thio, seleno or imino group, and
J is selected from the following structures, wherein the upper vertical line represents the bond with $R_1$ and the lower vertical line represents the bond with the nitrogen atom of the main chain of the polymer in the general formula I:

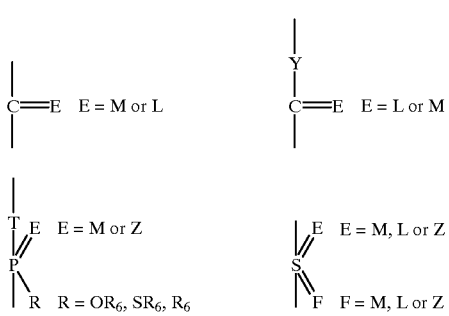

wherein $R_6$ is H, a substituent, (cyclo)alkyl, (cyclo)alkenyl, (cyclo)alkynyl, aroyl, heteroaroyl or heterocycle, with the proviso that at least one of the radicals R and $R_1$ in the compound of formula I is a radical derived from a natural or synthetic nucleobase (claim 1).

In a preferred embodiment, the process is characterised in that the fluorescent labels are fluorescein, Texas red, lissamine rhodamine, cyanine or rhodamine, the intercalators are psoralen, acridine, phenathroline, a phenanthroline/metal complex or ellipticine, the antibiotics are endiines, β-lactarns, tetracyclins, anthracyclins, polyethers, mitomycin-like antibiotics, phosphomycin-like antibiotics, macrolides, bleomycin-like antibiotics or an aminoglycoside, the minor groove binder is netropsin or distamycin, the polyamine is a spermidene-like polyamine, the antisense polymer is a (5'- or 3'-linked) DNA strand or a (5'- or 3'-linked) RNA strand or a phosphothioate, the peptide is linked at the N- or C-terminal, the antibody conjugate is selected from antibody conjugates that provide cell-specific uptake, are responsive to specific carrier systems or bring about endocytosis, the synthetic polymer is CPG, (controlled pore glass) a product which is a silica with a pore size of 25–300 nm, wang, a product which is a polystyrene based p-benzloxbenzyl alcohol resin, or Tentagel, a product which consists of about 30% of a porous matrix of approx. 1% cross-linked polystyrene on to which 70% PEG with an average molecular weight of 3000 g/mol has been grafted by oligomerization of oxirane, the natural nucleobases are adenine, thymine, guanine, cytosine or uracil and the synthetic nucleobases are pseudouracil, 5-propynyluracil, 5-hexenyluracil, 5-fluorocytidine, 5-hydroxymethyluracil, 5-methylcytidine, 5-bromocytidine and compounds of the following formulae

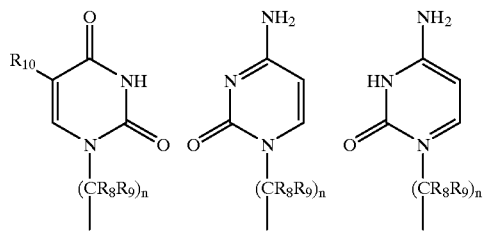

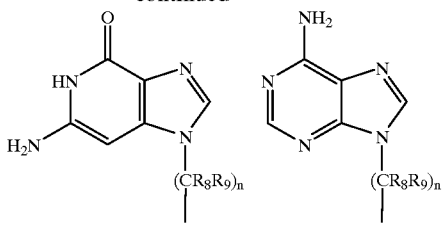

wherein $R_8$ and $R_9$ each independently of the other is H, (cyclo)alkyl, (cyclo)alkenyl, (cyclo)alkynyl, aroyl, heteroaroyl, heterocycle, chlorine or fluorine, $R_{10}$=fluorine, bromine, iodine, chlorine, alkynyl, (cyclo)alkyl, aroyl, heteroaroyl or H, and n=from 1 to 20, preferably from 1 to 10 and especially from 1 to 5, and wherein the side groups of the bases may be protected with protecting groups known to the person skilled in the art, such as, for example, tert-butylbenzoyl, p-methoxybenzyl, isobutanoyl.

All the functional units mentioned hitherto and hereinafter, such as antibiotics, groove binders, antisense molecules, steroids, antibody conjugates, intercalators and oligosaccharides can be bonded to the main polymer by a suitably constructed spacer. "Suitable" means containing at least one functional group of the Ugi reaction, such as an oxo, acid, amine or isocyano function. Alternatively, "suitable" can mean any other functional group by means of which the person skilled in the art joins two molecular units to one another.

The protecting groups PG are readily removable (temporary) protecting groups for amine groups customary per se. Otherwise, rigorous conditions would have to be used for their removal, which might result in undesirable secondary reactions or even in the disintegration of the reaction products. The protecting groups PG are preferably N-acyl derivatives, N-alkyl derivatives or azide groups, and special preference is given to N-acyl, N-sulphonyl, N-alkyl and N-silyl protecting groups, such as, for example, tert-Boc-, Alloc, Fmoc, Moz, Z, Tr, MMTr, DMTr, Pixyl and TBDMS protecting groups, and to salts of the amine.

Each of the radicals $R_5$ is independently of any others preferably a hydrogen atom, or an unsubstituted or substituted alkyl, aryl, cycloalkyl or alkoxyalkyl group or a heterocycle, especially a sterically undemanding group, such as alkyl, aryl, cycloalkyl, heterocycle and especially preferably a hydrogen atom; primary amines are generally more reactive than secondary amines [I. Ugi, Angew. Chem. 74, 9 (1962)].

The radicals U, W, K and Y each independently of the others preferably represents an unsubstituted or substituted alkyl, cycloalkyl or aryl group and especially preferably a methylene, ethylene, propylene, heptylene, octylene, nonylene, oxymethylene, oxyethylene, cyclohexyl or phenyl group, or a heterocycle.

Each of the indices a, b, m, n, o and p independently of the others is preferably an integer from 0 to 50, more especially from 0 to 20 or from 0 to 10, preferably from 0 to 5 and especially preferably from 0 to 3; most preferably a, b, p and o are 0 and m and n are 0, 1 or 2.

The radical Q is preferably at least an unsubstituted alkyl, aroyl or aryl group or an unsubstituted or substituted heterocycle and especially preferably a methylene, ethylene, propylene, oxymethylene, oxyethylene, dioxymethylene, 1,2-dioxyethylene, cyclohexyl or phenyl group, or N or a heterocycle.

According to the invention, compounds of formula V are therefore also provided. Preferred compounds of formula V have the following structure:

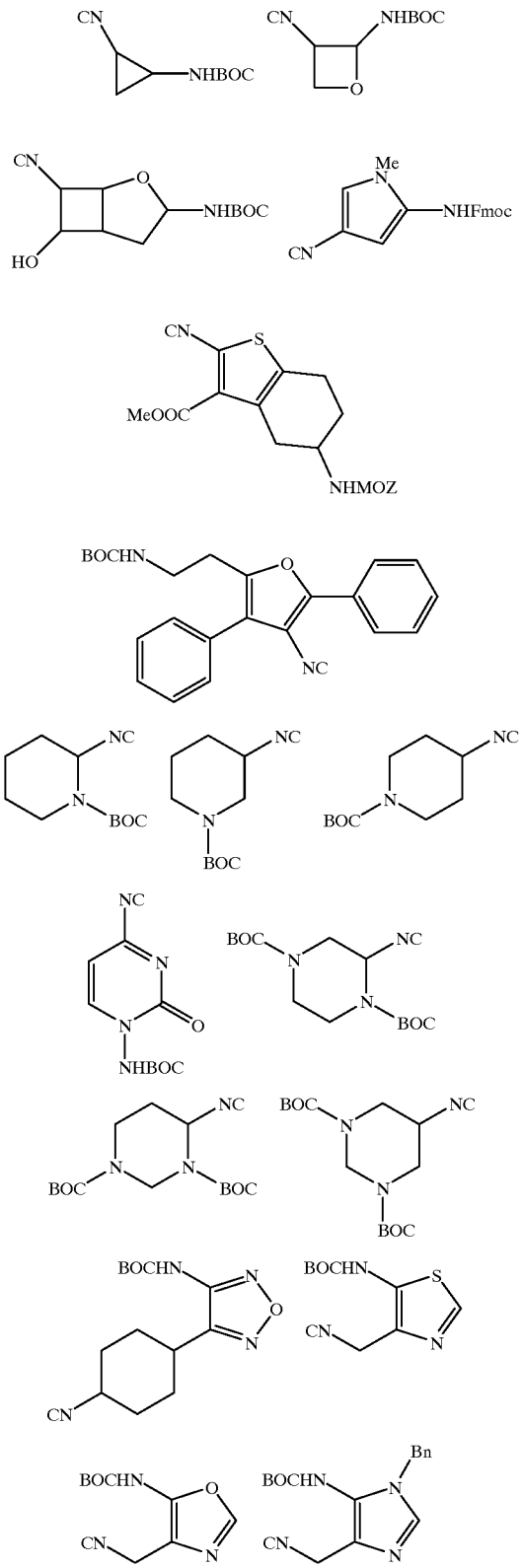

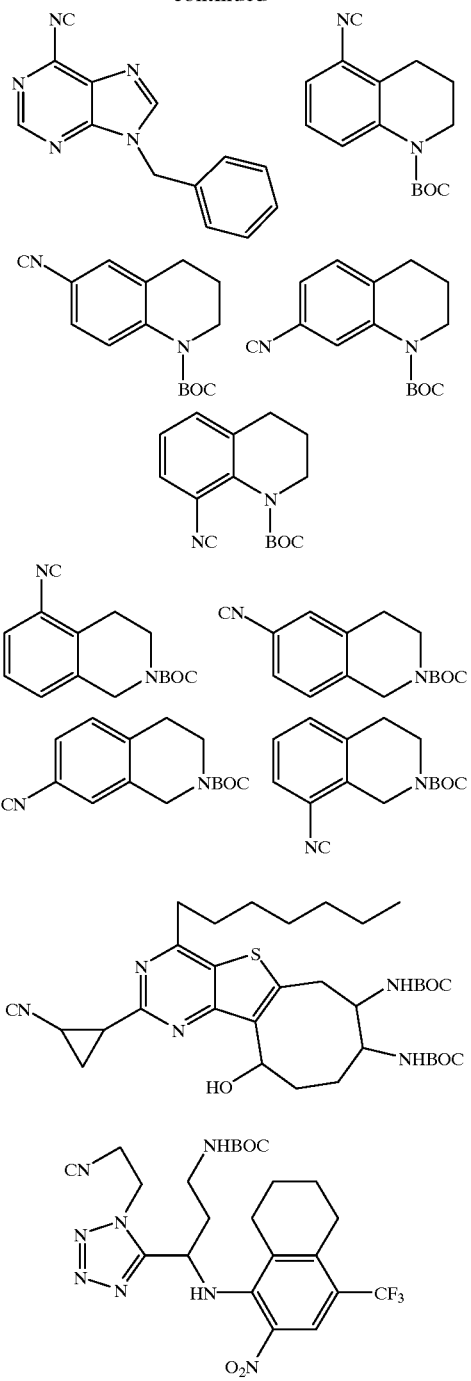

According to the invention, compounds of formula V can be prepared as follows: a compound of formula VII

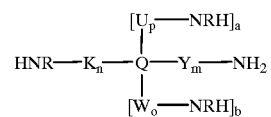

(VII)

is protected with the above-defined groups PG, which may be independent of one another, by customary processes, resulting in a compound of formula VIII

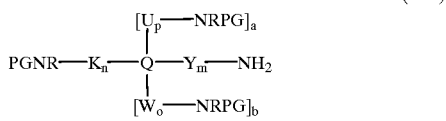

(VIII)

wherein the radicals and indices are as defined above, and then the compound of formula VIII is reacted by customary processes to form an isonitrile of formula V. Such customary processes for reacting compounds of formula VIII to form isonitriles of formula V are described, for example, in W. P. Weber, G. W. Gokel, *Tetrahedron Lett.* 1972, 1637; W. P. Weber, G. W. Gokel, I. K. Ugi, Angew. Chem. 84, 587 (1972); *Angew. Chem. Int. Ed. Engl.* 11, 530 (1972). Compounds of formula VII are commercially available.

In a further embodiment, the compound of formula VIII is reacted with customary formylation reagents to form a compound of formula IX:

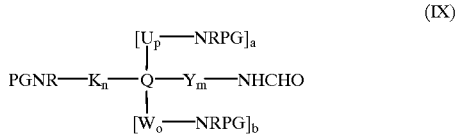

(IX)

which is then reacted under customary conditions to form a compound of formula V, the radicals and indices being as defined above (claim 4). Formylation with such customary formylation reagents is described, for example, in U. Sch öllkopf et al., *Liebigs Ann.* 89, 351–360 (1977). A customary process for reacting a compound of formula IX to form a compound of formula V is the elimination of water, as described, for example, by I. Hagedom, H. Tönjes, *Pharmazie* 11, 409 (1956); I. Ugi, R. Meyr, *Angew. Chem.* 70, 702 (1958); H. M. Walborsky, G. E. Niznik, *J. Org. Chem.* 37, 187 (1972); I. Ugi, W. Betz, U. Fetzer, K. Offermann, *Chem. Ber.* 94, 2814 (1961); I. Ugi, R. Obrecht, R. Herrmann, *Synthesis* 1985, 400–402; G. Gokel, D. Marquarding, P. Hoffmann, I. Ugi in Isonitrile Chemistry; I. Ugi (Ed.), Academic Press, New York, London 1971, 9. Preference is given to the use of phosphorus oxychloride and a suitable base, such as triethylamine or diisopropylamine.

In a further embodiment, starting from compounds of formula X

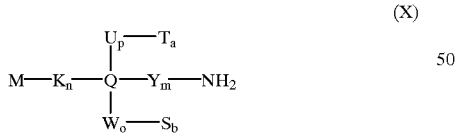

(X)

wherein the radicals and indices are as defined above, first the amine function is formylated, for example according to an above-mentioned method, and then one or more of the functionalities M, T and S, which each independently of the others represents a halogen or a hydroxy function, preferably chlorine, bromine or hydroxyl, is/are converted into one or more azide functions according to a customary process, those azides are converted into the corresponding amines according to a customary process and the amines are then provided with above-mentioned protecting groups by customary processes in order to obtain compounds of formula IX. The compounds of formula X can also first be converted, after formylation and conversion of the groups M, T and S into the corresponding azides, for example according to above-mentioned methods, into the corresponding isonitriles, and the azide functions can be converted into amines according to a customary process and then provided with above-mentioned protecting groups in order to obtain compounds of formula V.

According to the invention the use of compounds of formula V is also disclosed:

For use of compounds of formula V, the compounds according to the invention may first be reacted, for example in the context of a customary MCR, such as, for example, a Ugi- or Passerini-type reaction, with 2, 3 or more further compounds, such as aldehydes, amines and carboxylic acids. Thereafter, by removal of at least one protecting group at least one functional group, such as a primary or secondary amine or a hydrazine group, can be freed, which can then be reacted further, for example in the context of a further MCR as described above or in the context of a classic two-component reaction. As a result it is also possible to produce a large number of highly complex molecules by repeated use of the compounds according to the invention. By the selective removal of protecting groups and the use of precisely defined reactants, it is also possible to synthesise a large number of molecules that would otherwise be very difficult or impossible to obtain. The compounds according to the invention can also be used in the production of peptide nucleic acid polymers (PNA).

In the description and claims the following definitions are used as a basis:

alkyl or "alk" or "alkane", including as word components:
chain length C1 to C100, preferably C1 to C20, more especially C1 to C10, still more especially C1 to C6 and most especially C1 to C4, linear or branched, substituted (as defined below) or unsubstituted, cycloalkyl or cycloalkane: ring size C3 to C20, preferably C3 to C9, more especially C3 to C7, most especially C5, C6 or C7, substituted (as defined below) or unsubstituted, alkenyl: alkyl (having at least 2 C atoms) or cycloalkyl containing from 1 to 5, preferably 1 or 2, conjugated or unconjugated double bonds, alkynyl: alkyl (having at least 2 C atoms) or cycloalkyl containing from 1 to 5, preferably 1 or 2, conjugated or unconjugated triple bonds, heterocycle: 3- to 7-membered, preferably 5- or 6-membered, heterocycles having 1, 2, 3 or optionally 4 hetero atoms, such as N, O or S, such as, for example, substituted (as defined below) or unsubstituted oxirane, thiirane, aziridine, oxaziridine, oxetane, thietane, azetidine, tetrahydrofuran, dihydrofuran, tetrahydrothiophene, dihydrothiophene, pyrrolidine, dihydropyrrole, 1,3-dioxolane, 1,3-dithiolane, imidazolidine, oxazolidine, thiazolidine, 2H-pyran, 4H-pyran, tetrahydropyran, 2H-thiopyran, 4H-thiopyran, tetrahydrothiopyran, piperidine, morpholine, 1,4-dioxin, 1,4-dioxane, 1,4-dithiine, 1,4-dithiane, piperazine, oxepan, thiepan, thiepin, 1H-azepin, 2H-azepin, azepan, aroyl: substituted (as defined below) or unsubstituted benzene, naphthalene, anthrazene, biphenyl, triphenyl, azulene, ferrocene, cyclopropenylium, heteroaroyl: 5- or 6-membered heterocyclic aromatic heterocycles having 1, 2 or 3 hetero atoms, such as, for example, substituted (as defined below) pyrrole, furan, thiophene, pyrazole, isoxazole, isothiazole, imidazole, oxazole, thiazole, 1,2,4-triazole, 1,2,4-oxadiazole, 1,2, 4-thiadiazole, 1,2,5-oxadiazole, 1,2,5-thiadiazole, tetrazole, pyridine, pyrylium, thiapyrylium, pyridazine, pyrimidine, pyrazine, 1,2,3-triazine, 1,2,4-triazine, 1,3,5-triazine, 1,2,3,4-tetrazine, 1,2,3,5-tetrazine, 1,2,4,5-tetrazine, indole, cumarone, thionaphthene, carbazole, bibenzofuran, dibenzothiophene, 1H-indazole, indoxazole, benzo[d]isothioazole, anthranil, benzimidazole, benzoxazole, benzothiazole, benzotriazole, quinoline, isoquinoline, benzopyrylium, thiabenzopyrylium, acridine, benzo[g]quinoline, benzo[g]isoquinoline, benzo[c]quinoline, cinnoline, phthalazine, quinazoline, quinoxaline, phenazine, benzo[g]cinnoline, benzo[g]quinazoline, benzo[g]quinoxaline, 1,5-naphthyridine, 1,6-naphthyridine, 1,7-naphthyridine, 1,8-naphthyridine, 2,6-naphthyridine, 2,7-naphthyridine, 1,7-phenanthroline, 1,8-phenanthroline, 1,9-phenanthroline, 1,10-phenanthroline, indolizine, 4H-quinolizine, carboline, ergoline, purine, pteridine, alloxazine, flavin, substituent or "substituted by": —H, —OH, —$R_a$, —O-(cyclo)alkyl, —O-aryl, —O-heteroaroyl, —O-heterocycle, —$NH_2$, —$NO_2$, —CN, —$N_3$, —$CNR_aNR_bR_c$, —$NR_aR_b$, $NR_aR_bR_c^+$, fluorine, chlorine, bromine, a-, b- to w-amino acid esters, —$NR_aCOR_b$, —$NR_aCOXR_b$ (X=—O, —NR, —$PO_{0,2,3,4}R$, —$SO_{0,1,2,4}R$, —$NR_aNR_bR_c$), —$COR_a$, —$COOR_a$, —$OCOOR_a$, —$CONR_aR_b$, —$OCONR_aR_b$, —$NRCCONR_aR_b$, —$R_a$—O—$R_b$, —$R_c$—$NR_aR_b$, —$R_a$—S—$R_b$, —$R_a$—SO—$R_b$, —$R_a$—$S(O)_2$—$R_b$, —$OR_a$—O—$R_b$, —$NR_aR_b$—O—$R_c$, —$SO_2R_a$, —$SO_{1,2,3,4}R_a$—$OR_b$, —$COR_a$—$OR_b$, —$COOR_a$—O—$R_b$, —$OCOR_a$—O—$R_b$, —$OCOOR_a$—O—$R_b$, —$NR_bCOR_a$—O—$R_b$, —$CONR_aR_b$—O—$R_c$, —$OCONR_aR_b$—O—$R_c$, —$NR_cCONR_aR_b$—O—$R_d$, —$NR_aCOR_b$—O—$R_c$, —$OR_a$—S—$R_b$, —$NR_aR_b$—S—$R_c$, —$SO_{1,2,3,4}R_a$—S—$R_b$, —$COR_a$—S—$R_b$, —$OCOR_a$—S—$R_b$, —$OCOR_a$—S—$R_b$, $NR_aCOR_b$—S—$R_c$, —$CONR_aR_b$—S—$R_c$, —$NR_aCONR_bR_c$—S—$R_d$, —$OR_a$—$NR_bR_c$, —$NR_aR_b$—$NR_cR_d$, —$SO_{1,2,3,4}R_b$—$NR_bR_c$, —$COR_a$—$NR_bR_c$, —$COOR_a$—$NR_bR_c$, —$OCOR_a$—$NR_bR_c$, —$OCOOR_a$—$NR_bR_c$, —$NR_aCONR_bR_c$—$NR_d$, —$NR_aCOOR_b$— $NR_cR_d$, —$OCONR_aR_b$—$NR_cR_d$, —$NR_aCONR_bR_c$—$NHR_d$, —$NR_aCOOR_b$—$NR_cR_d$, —$POOR_aOR_b$, —$NR_cPOOR_aOR_b$, wherein $R_a$, $R_b$, $R_c$ and $R_d$ each independently of the others may be, as defined above, (cyclo)alkyl, alkenyl, alkynyl, aroyl, heteroaroyl, a heterocycle, aralkyl, aralkenyl or perhaloalkyl and wherein $R_a$, $R_b$, $R_c$ and $R_d$ may be substituted.

The process according to the invention accordingly relates to the preparation of monomers, oligomers and polymers having nucleobases as side groups, especially of peptide nucleic acid (PNA) and variants thereof, by means of multicomponent reactions (MCRs), especially isocyanide-based MCRs, such as the Ugi reaction. That process does not involve using monomers as in conventional processes, but utilises smaller building blocks than have hitherto customarily been used, so-called sub-monomers. The process presented here allows improved synthesis of the PNA variants described hitherto and inter alia rapid synthesis of novel variants, not previously described, having potentially improved and/or novel properties. Because of the multicomponent nature of this process, it is possible to incorporate simultaneously a large number of different types of radicals in a quasi-combinatorial manner, for example into the polyamide backbone of the PNA, and also, using suitable synthesis building blocks described below, to synthesise $(PNA)_2$, (PNA)(DNA), (PNA)(RNA), (PNA)(peptide), $(PNA)_2$(DNA), (PNA)((oligo)saccharide) and $(PNA)_2$(DNA)(peptide) chimera etc., and to synthesise modified PNA polymer backbones, such as, for example, thioamides. Relatively short oligomers prepared according to the described process or even monomers are potentially pharmacologically or agrochemically relevant active ingredients.

The process described here is based on isocyanide-based multicomponent reactions (MCRs) of the four-component condensation or Ugi reaction type (Isocyanide Chemistry, (I. Ugi, ed.), Wiley, New York, 1971; I. Ugi, R. Karl, in: Comprehensive Organic Synthesis), (B. M. Trost, C. H. Heathcock (ed.), Vol. II, 1083–1109, Pergamon Press, New York 1991). In that reaction, the four starting components isocyanide, oxo compound (aldehydes or ketones), amine-like compounds (e.g. ammonia, primary amines, secondary amines, hydrazine and derivatives, hydroxylamine and derivatives) and suitable acid components (e.g. carboxylic acids, carbonic acid monoesters, water, thiosulphate, hydrogen selenide, hydrazoic acid, cyanic acid, thiocyanic acid) react to form uniform products, the central basic structure of which depends essentially upon the nature of the acid component. Remarkably the radicals of the individual components can be varied within wide limits without loss of reactivity. For example, sterically demanding starting materials or small, aromatic, heteroaromatic, as well as aliphatic or heterocyclic, electron-attracting or electron-repelling starting materials react equally well in the Ugi reaction. Related isocyanide-based MCRs are the Passerini reaction (I. Ugi in Isocyanide Chemistry, (I. Ugi, ed.), Wiley, New York, 1971) as well as a number of heterocycle syntheses (S. Marcaccini, T. Torroba, OPPI, 143).

Compounds suitable for use according to the invention have for example the following structures:

imines:

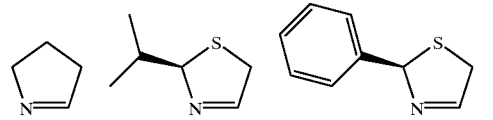

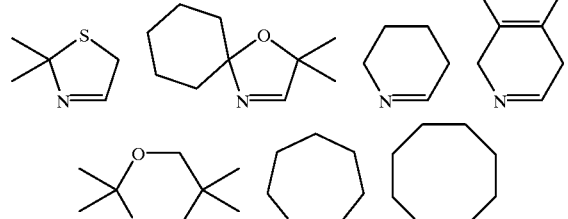

isocyanides:

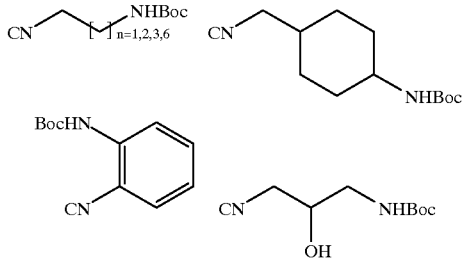

-continued carboxylic acids:

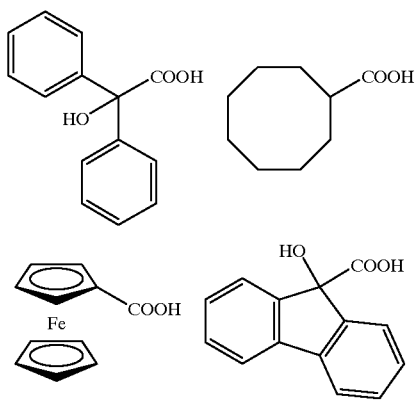

Those compounds can be used, for example, in the following reaction:

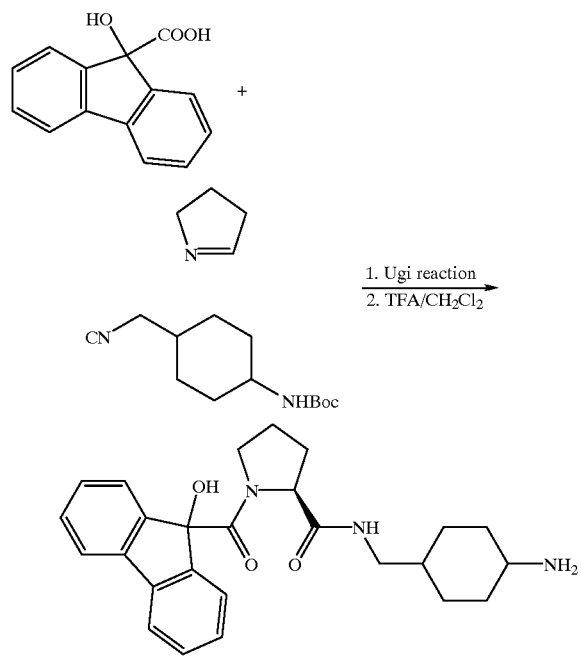

By means of the process according to the invention, homo- and hetero-polymers of general formula I can be prepared as shown in Scheme I Scheme I Step I:

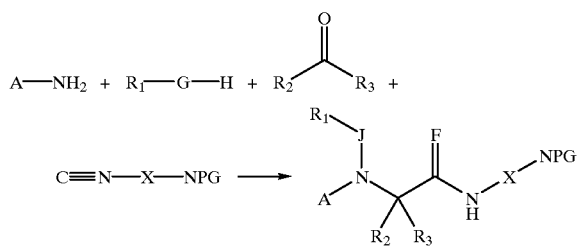

-continued

Step II:

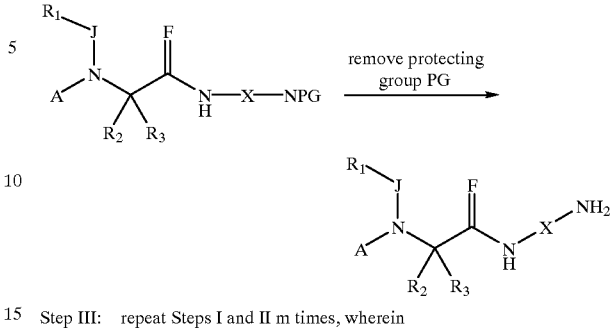

Step III: repeat Steps I and II m times, wherein

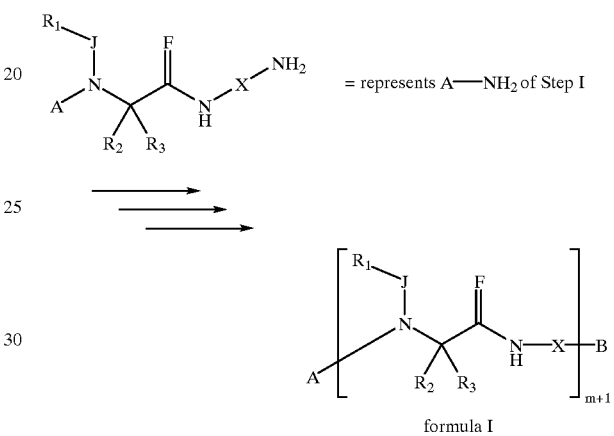

formula I

The process for preparing homo- and hetero-polymers of general formula I is characterised in that four different compounds having suitable functional groups are reacted with one another optionally synchronously optionally several times. After the first step, that is to say after the optionally synchronous reaction of the compounds II, III, IV and V, the product of each preceding step is then used instead of the compound of formula II. In order to obtain heteropolymers, the compounds do not have the same radicals or functional groups in all the synthesis steps.

The syntheses of the classes of compound shown by formula I can be carried out on surfaces, in liquid phase or on polymeric carriers.

Synthesis of the compounds of formula I can also be carried out on so-called "chips":

a substrate is prepared to which there is applied in a first region a compound, selected from compounds of formulae II, III, IV and V, having protecting groups that can be removed by activators;

that step is optionally repeated on other regions of the surface in each case with a different compound of compounds II, III, IV and V having a corresponding protecting group or groups, a region of the surface which may have one or more of the compounds II, III, IV and V is exposed to an activator in order to remove at least one protecting group, that region is exposed to a compound of formula II, III, IV or V which, in turn, has a photo-sensitive protecting group, and that step is optionally repeated in other regions with any desired combination of the compounds of formulae II, III, IV and V.

The substrate may be a polymerised Langmuir Blodgett film, a functionalised glass, germanium, silicon, polymers, (poly)tetrafluoroethylene, polystyrene, gallium arsenite or a combination thereof;

as activators there come into consideration ion beams, electron beams, trays, X-rays, ultraviolet rays, light, infrared rays, microwaves, electric currents, radio waves and combinations thereof.

As photo-sensitive protecting groups there come into consideration, for example, orthonitrobenzyl derivatives, 6-nitroveratryloxycarbonyl, 2-nitrobenzyloxycarbonyl, cinnamoyl derivatives and mixtures thereof.

Furthermore, in respect of the substrates to be used, the activators to be used, the photo-sensitive protecting groups and the conditions under which the individual steps are carried out, reference is made to the full contents of the following specifications: WO 90/15070, WO 91/07087, WO 92/10092, EP 0 728 520.

Advantages of PNA chips over DNA chips are inter alia substantially improved detection of mutations in the DNA being studied and the greater stability of PNA chips compared with DNA chips.

The synthesis of a DNA or RNA strand in A is effected according to processes known to the person skilled in the art, such as the triester method, the H-phosphonate method or phosphoamidite method, preferably according to the standard phosphoamidite method according to Caruthers (M. H. Caruthers et al., J. Am. Chem. Soc., 103, 3185 (1981)). The following compound can be used as linker building block for binding to the conventional PNA synthesised in Scheme I:

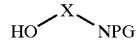

wherein X is an optionally substituted alkyl, cycloalkyl, (cyclo)alkenyl, (cyclo)alkynyl, aroyl, heteroaroyl or heterocycle, PG is a protecting group that must be compatible with a synthesised DNA or RNA or other antisense polymer strand, and is, for example, dimethoxytrityl, Fmoc, Moc, 5-dimethoxybenzyl carbamate, an o- or m-nitrophenyl carbamate such as Nvoc or 3,4-dimethoxy-6-nitrobenzyl carbamate or phenyl(o-nitrophenyl)methyl carbamate.

The synthesis of a peptide strand in A is effected according to processes known to the person skilled in the art, such as the Merrifield method (E. Atherton, R. C. Sheppard, Solid Phase Peptide Synthesis—A Practical Approach, IRL Press, New York, 1989). Any natural or synthetic N-protected amino acid can be used as linker building block for binding to the conventional PNA synthesised in Scheme I. After removal of the protecting group, a PNA strand adjoining the peptide strand is produced according to the methodology outlined in Scheme I.

The synthesis of an oligosaccharide strand in A is effected according to processes known to the person skilled in the art, such as, for example, the Schmidt trichloroacetimidate method or epoxide ring opening (P. Collins, R. Ferrier, Monosaccharides, Wiley, New York 1996, 415–430). There may be used as linker building block for binding to the conventional PNA synthesised in Scheme I, for example,

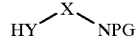

wherein X is an optionally substituted alkyl, cycloalkyl, (cyclo)alkenyl, (cyclo)alkynyl, aroyl, heteroaroyl or heterocycle, Y is a nucleophile, such as S, O, NR wherein R=an optionally substituted alkyl, cycloalkyl, (cyclo)alkenyl, (cyclo)alkynyl, aroyl, heteroaroyl, heterocycle or —CHPL, wherein P and L each independently of the other represents —CN, —NC, —COOR, —PO(OR)$_2$ or —SO$_2$R, PG is a protecting group that must be compatible with a synthesised oligosaccharide strand and is, for example, dimethoxytrityl, Fmoc or Pmoc or Nvoc.

The group X in formula V can be a starting point for a further DNA, RNA, PNA or peptide synthesis or another oligomer or polymer synthesis.

The synthesis of a DNA or RNA strand in X is effected according to processes known to the person skilled in the art, such as the triester method, the H-phosphonate method or the phosphoamidite method, preferably according to the standard phosphoamidite method according to Caruthers (M. H. Caruthers et al., J. Am. Chem. Soc., 103 3185 (1981)). As linker building block for binding to the conventional PNA synthesised in Scheme I there can be used, for example, the following compound of the general formula CN—X—NPG:

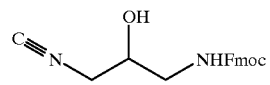

wherein the hydroxy group serves as anchor for the subsequent RNA/DNA or phosphothioate antisense synthesis.

The synthesis of a peptide strand or of a further PNA strand in X is effected according to processes known to the person skilled in the art, such as the Merrifield method (E. Atherton, R. C. Sheppard, Solid Phase Peptide Synthesis—A Practical Approach, IRL Press, New York, 1989) or the method described in Scheme I (PNA). As linker building block there may be used any isocyanide having a protected amine function, such as, for example, the following trifunctional isocyanide of the general formula CN—X—NPG:

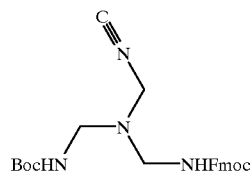

After the Ugi reaction with the isocyanide is complete, the Fmoc protecting group, for example, is removed and a peptide or PNA strand is synthesised. After completion of the side chain synthesis, the PNA of the main chain is synthesised further by removal of the Boc protecting group.

The synthesis of an oligosaccharide strand in X is effected according to processes known to the person skilled in the art, such as, for example, the Schmidt trichloroacetimidate method or epoxide ring opening (P. Collins, R. Ferrier, Monosaccharides, Wiley, N.Y. 1996, 415–430). As linker building block there may be used, for example, the following trifunctional isocyanide of the general formula CN—X—NPG:

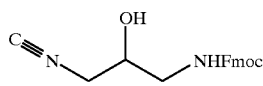

in which case the glycolisation takes place at the free hydroxy function, or the following isocyanide of the general formula CN—X—NPG:

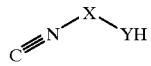

in which case the glycolisation takes place via the nucleophilic Y group,

X represents substituted alkyl, cycloalkyl, (cyclo)alkenyl, (cyclo)alkynyl, aroyl, heteroaroyl, heterocycle, Y is a nucleophile such as S, O, NR wherein R=substituted alkyl, cycloalkyl, (cyclo)alkenyl, (cyclo)alkynyl, aroyl, heteroaroyl, heterocycle, or —CHPL, wherein P and L each independently of the other represents —CN, —NC, —COOR, —PO(OR)$_2$ or —SO$_2$R.

The synthesis of a DNA or RNA strand in B is effected according to processes known to the person skilled in the art, such as the trester method, the H-phosphonate method or the phosphoamidite method, preferably according to the standard phosphoamidite method according to Caruthers (M. H. Caruthers et al., J. Am. Chem. Soc., 103 3185 (1981)). As linker building block for binding to the conventional PNA synthesised in Scheme I there may be used, for example, the following compound of the general formula CN—X—NPG:

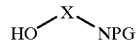

wherein X is substituted alkyl, cycloalkyl, (cyclo)alkenyl, (cyclo)alkynyl, aroyl, heteroaroyl or heterocycle, PG is a protecting group that must be compatible with a synthesised DNA or RNA or other antisense polymer strand, and is, for example, dimethoxytrityl, Fmoc, Moc, 5-dimethoxybenzyl carbamate, or an o- or m-nitrophenyl carbamate, such as Nvoc or 3,4-dimethoxy-6-nitrobenzyl carbamate or phenyl(o-nitrophenyl)methyl carbamate, wherein the hydroxy group serves as anchor for the subsequent RNA/DNA or phosphothioate antisense synthesis.

Liquid phase methods are preferably used for the synthesis of large amounts of relatively short oligomers, whilst solid phase methods are suitable for the synthesis of relatively small to relatively large amounts of long oligomers, and surface methods are suitable for the synthesis of small amounts of long oligomers.

Experimental Conditions for Liquid Phase Synthesis

In liquid phase, the amine component is reacted with the oxo component, the acid component and a suitably substituted amine-protected isocyanoamine component according to Scheme I. Advantageously one equivalent of each of the four different components is added together and thus caused to react. Advantageously the amine and the oxo components are also to be pre-condensed to form the Schiff base. Suitable solvents are aprotic-polar and non-polar as well as protic-polar solvents. Because of the solubility properties of the nucleobase acid components, suitable solvents are inter alia protic and protic-polar solvents, such as, for example, alcohols such as water, methanol, ethanol, propanol, ethylene glycol, glycerol, trifluoroethanol, and aprotic-polar solvents, such as, for example, pyridine, N-methylmorpholine, methylene chloride, chloroform, dimethylformamide, dimethyl sulphoxide, acetonitrile, ethylene glycol dimethyl ether, or mixtures thereof, such as, for example, ethylene glycol dimethyl ether/glycerol or a solvent promoting Schiff base formation, such as trimethyl orthoformate. Acylation catalysts, such as, for example, pyridine or 4-dimethylaminopyridine, have proved to promote reaction in the Ugi reaction. Lewis-acids, such as ZnCl$_2$, TiCl$_4$, ZrCp$_2$Cl$_2$, etc., have also proved to promote reaction in the Ugi reaction. The reaction temperature may be from −20° C. to +100° C., but preferably from 10 to 40° C. The reaction time lasts from seconds to several days depending upon the reactivity of the components. Advantageously the Ugi reaction is carried out in concentrated form, that is to say the concentrations of the individual components are from 0.1M to 4M.

Experimental Conditions for Solid Phase Synthesis

Polymers for the solid phase synthesis of nucleobase polymers may be, for example, polystyrene, polyethylene glycol, polyethylene glycol/polystyrene copolymers, polyacrylamide, controlled porous glass (CPG), Teflon, polyethylene, polypropylene, nylon, cellulose. Suitable linkers are, for example, aminomethyl, 4-methylbenzhydrylamine (MBHA), 4-(2',4'-dimethyloxyphenyl-Fmoc-aminomethyl)-phenoxyacetamido-norleucylaminomethyl (Rink amide AM), 4-(2',4'-dimethyloxyphenyl-Fmoc-aminomethyl)-phenoxyacetamido-norleucyl-MBHA (Rink amide MBAH), 4-(2',4'-dimethyloxyphenyl-Fmoc-aminomethyl)-phenoxy (Rink amide), 9-Fmoc-amino-xanthen-3-yloxy (Sieber amide), hydrazine-2-chlorotrityl, 4-sulphamylbenzoyl AM, 4-sulphamylbutyryl AM, bis-(2-aminoethyl)-ether trityl, 1,3-bis-(aminomethyl)-phenyltrityl or resins loaded with N-terminal-protected amino acids.

The synthesis starting materials may be present in a wide variety of solvents, mentioned in the above section, that are compatible with the swelling properties of the polymers. Based on the load on the polymer, the starting materials are used in an excess of from 2 to 20. Lewis acids, such as ZnCl$_2$, TiCl$_4$, ZrCp$_2$Cl$_2$, etc., have also proved to promote reaction in the Ugi reaction. The reaction temperature can be from −20° C. to +100° C., but preferably from 10 to 40° C. The reaction time lasts from seconds to several days depending upon the reactivity of the components. Advantageously the Ugi reaction is carried out in concentrated form, that is to say the concentrations of the individual components are from 0.1M to 4M.

Experimental Conditions for Synthesis on Surfaces

The surfaces must be modified for the polymer synthesis by linkers. Possible surfaces are, for example, glass surfaces, polymer surfaces, such as Teflon, polyethylene, polypropylene, nylon, cellulose. Advantageously photo-protecting groups are attached to the surface by way of a linker. By removing the protecting groups from a selective region of the surface, it is possible to commence with the process for the synthesis of PNAs described in Scheme I. Advantageously all the protecting groups of the individual components are photo-protecting groups, as shown in the following illustration.

Advantages and Possible uses of the Described Invention

The process described here for the preparation of polymers having nucleobases as side groups using multicomponent reactions surpasses all processes described hitherto in terms of the effectiveness of the synthesis and the accessiblity of novel PNAs. The previously described PNA variants have many disadvantages for use as antisense and antigen active ingredients. The process put forward here can be used most effectively to seek novel improved variants. Since in previous processes monomers polymerised to the PNAs had to be produced via a number of steps, the number of variations obtainable was substantially smaller compared with the process presented here. In the process presented, a monomer unit consisting of four different components is produced in one step. Since many of the starting materials of the Ugi reaction are available commercially or can readily be obtained simply in one or two steps from commercially available compounds, it is possible to prepare substantially more variants in the same period of time and at a comparable cost.

Potent virostatics or carcinostatics can be prepared using the monomer or di- and tri-mers prepared according to the combinatory process presented here.

EXAMPLES

The abbreviations used are listed hereinbelow.

| | |
|---|---|
| Alloc | allyloxycarbonyl |
| Boc | tert-butyloxycarbonyl |
| $Boc_2O$ | pyrocarbonic acid di-tert-butyl ester |
| DCM | dichloromethane |
| DMF | dimethylformamide |
| Dmt | 4,4'-dimethoxytriphenylmethyl |
| Fmoc | 9-fluorenylmethoxycarbonyl |
| FmocONSu | N-(9-fluorenylmethoxycarbonyloxy)-succinimide |
| Mmt | 4-methoxytriphenylmethyl |
| Moz | p-methoxybenzyloxycarbonyl |
| Pixyl | 9-(9-phenyl)xanthenyl |
| TBDMS | tert-butyldimethylsilyl |
| TFA | trifluoroacetic acid |
| Trt | triphenylmethyl |
| Z | benzyloxycarbonyl |

General Procedure for the Synthesis of 2-tritylamino-ethylisocyanide Radicals (X)

Preparation of 2-tritylethylenediamines 40 mmol of the trityl chloride in question (triphenylmethyl chloride, 4-methoxytriphenylmethyl chloride, 4,4'-dimethoxytriphenylmethyl chloride) dissolved in 500 ml of THF are slowly added dropwise to 12.20 g (200 mmol) of ethylenediamine in 500 ml of THF at room temperature. The mixture is then stirred at room temperature for 12 hours, the solvent is removed using a rotary evaporator, and the oily slightly yellow to orange residue is taken up in 500 ml of ethyl acetate and extracted three times with 250 ml of saturated sodium chloride solution each time. The organic phase is dried with sodium sulphate. After removal of the solvent, the amine in quesfion is obtained in the forrn of an oil or foam in yields of from 50 to 95%.

N-tritylethylenediamine; $C_{21}H_{22}N_2$ (288.42); $R_F$=0.21 (DCM/MeOH 5:1, v/v); spot stains with ninhydrin spray or with HCl vapour); N-(4-monomethoxytrityl) ethylenediamine; $C_{22}H_{24}N_2O$ (332.45); $R_F$=0.21 (DCM/ MeOH 5:1, v/v); spot stains with ninhydrin spray or with HCl vapour); N-(4,4'-dimethoxytrityl)ethylenediamine; $C_{23}H_{26}N_2O_2$ (362.48); $R_F$=0.22 (DCM/MeOH 5:1, v/v); spot stains with ninhydrin spray or with HCl vapour).

Preparation of 2-tritylaminoethylformamides 190 mmol of the amine in question are refluxed in 300 ml of ethyl formate for 12 hours (oil bath temperature 75° C.). After removal of the excess ester using a rotary evaporator, the formamide in question is obtained in the form of a stable or tacky, yellow to orange foam. The yields are from 80 to 95%.

2-tritylaminoethylformamide; $C_{22}H_{22}N_2O$ (330.42); $R_F$=0.87 (DCM/MeOH 5:1, v/v); spot stains with ninhydrin spray or with HCl vapour); 2-(4-monomethoxytrityl) aminoethylformamide; $C_{23}H_{24}N_2O_2$ (360.46); $R_F$=0.86 (DCM/MeOH 5:1, v/v); spot stains with ninhydrin spray or with HCl vapour); $^1$H NMR ($CDCl_3$, 250.133 MHz):=1.70 (br s, 1 H); 2.32 (tr, 2H, J=6.0 Hz); 3.37 (m, 2H); 3.76 (s, 3H); 5.99 (br s, 1H); 6.78–7.49 (m, 14H); 8.17 (s, 1H). $^{13}$C NMR ($CDCl_3$, 62.896 MHz):=38.7 ($CH_2$); 43.1 ($CH_2$); 55.2 ($CH_3$); 70.2 (C); 113.2 (CH); 126.4 (CH); 127.9 (CH); 128.3 (CH); 129.7 (CH); 137.8 (C); 145.9 (C); 158.0 (C); 164.7 (CHO). 2-(4,4'-dimethoxytrityl)aminoethylformamide; $C_{24}H_{26}N_2O_3$ (390.49); $R_F$=0.92 (DCM/MeOH 5:1, v/v); spot stains with ninhydrin spray or with HCl).

Preparation of 2-tritylaminoethylisonitriles 180 mmol of the formamide in question are dissolved in 250 ml of methylene chloride. After the addition of 400 mmol of TEA, the mixture is cooled to 0° C., and 180 mmol of phosphorus oxychloride are slowly added dropwise thereto, and the mixture is stirred at that temperature for a further two hours. At 20° C., 340 mmol of sodium carbonate in 150 ml of water are then slowly added with vigorous stirring and the mixture is stirred at room temperature for a further 30 minutes. The aqueous phase is diluted to 400 ml and extracted twice with 150 ml of DCM each time. After washing of the organic phase with saturated NaCl solution, drying over potassium carbonate and removal of the solvent, the isonitriles in question are obtained in the form of a foam in a yield of 85–95%.

2-tritylaminoethylisocyanide; $C_{22}H_{20}N_2$ (312.42); $R_F$=0.90 (DCM/MeOH 5:1, v/v); spot stains with ninhydrin spray or with HCl vapour); 2-(4-monomethoxytrityl) aminoethylisocyanide; $C_{23}H_{22}N_2O$ (342.44); $R_F$=0.89 (DCM/MeOH 5:1, v/v); spot stains with ninhydrin spray or with HCl vapour); 2-(4,4'-dimethoxytrityl) aminoethylisocyanide; $C_{24}H_{24}N_2O_2$ (372.47); $R_F$=0.95 (DCM/MeOH 5:1, v/v); spot stains with ninhydrin spray or with HCl vapour);

General Procedure for the Synthesis of N-acylethylisocyanides

N-(tert-butyloxycarbonyl)ethylenediamine 0.25 mol of $Boc_2O$ in 500 ml of THF is added dropwise at room temperature within a period of 12–48 hours to a solution of 2.0 mol of ethylenediamine in 700 ml of THF. The solution is decanted off from the precipitated solid and the solvent is removed. The residue and the precipitated solid are dissolved in 500 ml of water and the resulting suspension is filtered. The aqueous phase is extracted three times with 150 ml of DCM each time, washed with concentrated NaCl solution, dried and concentrated using a rotary evaporator, resulting in 36 g of an oil (90% based on $Boc_2O$).

N-(tert-butyloxycarbonyl)aminoethylformamide 21.8 mmol of N-(tert-butyloxycarbonyl)ethylenediamine are dissolved in 50 ml of ethyl or methyl formate, and p-toluenesulphonic acid is added as catalyst. This mixture is refluxed for 12 hours. After concentration of the solution using a rotary evaporator, the residue is taken up in 100 ml of DCM or ethyl acetate, washed twice with water and dried, and the solvent is removed. 3.86 g of an oil are obtained, which gradually crystallises out (94% yield).

Mp: 84–86° C.;
2-(N-tert-butyloxycarbonyl)aminoethylisonitrile

The isonitrile is prepared according to the above procedure, resulting virtually quantitatively in an oil, which gradually crystallises out.

$^1$H NMR (250 MHz, CDCl$_3$): 1.42 (s, 9H, CH$_3$), 2.92 (m, 2H, CH$_2$), 3.40 (m, 2H, CH$_2$), 5.00 (s, 1H, NH). $^{13}$C NMR (62 MHz, CDCl$_3$): 28.1 (CH$_3$); 38.1 (t, $^1$J=7.5 Hz, CH$_2$—NC), 39.0 (CH$_2$—NH), 80.0 (C), 155.8 (CO), 156.2 (t, $^1$J=5.5 Hz, NC).

The following compounds are prepared in analogous manner according to the above procedure:
3-(N-tert-butyloxycarbonyl)aminopropylisonitrile $^1$H NMR (250 MHz, CDCl$_3$): 1.44 (s, 9H, CH$_3$), 1.89 (m, 2H, CH$_2$), 3.26 (q, 2H, $^3$J=6.2 Hz, CH$_2$), 3.46 (m, 2H, CH$_2$), 4.92 (s, 1H, NH). $^{13}$C NMR (62 MHz, CDCl$_3$): 28.2 (CH$_3$); 29.4 (CH$_2$), 38.1 (t, $^1$J=7.6 Hz, CH$_2$—NC), 39.0 (CH—NH), 79.4 (C), 155.9 (CO), 156.4 (t, $^1$J=5.3 Hz, NC).
6-(N-tert-butyloxycarbonyl)aminohexylisonitrile $^1$H NMR (250 MHz, CDCl$_3$): 1.36 (m, 6H, CH$_2$), 1.44 (s, 9H, CH$_3$), 1.89 (m, 2H, CH$_2$), 3.27 (m, 2H, CH$_2$), 3.47 (m, 2H, CH$_2$), 5.02, 4.92 (2s, 1 H, NHCO-rotamers). $^{13}$C NMR (62 MHz, CDCl$_3$): 28.2 (CH$_3$), 28.3 (CH$_2$), 29.5 (CH$_2$), 30.5 (CH$_2$), 38.2 (t, $^2$J=6.7 Hz, CH$_2$—NC), 39.0 (CH$_2$—NH), 77.4 (C), 156.2 (CO), 156.4 (t, $^2$J=5.3 Hz, NC).
8-(N-tert-butyloxycarbonyl)aminooctylisonitrile $^1$H NMR (250 MHz, CDCl$_3$): 1.31 (m, 10H, CH$_2$), 1.44 (s, 9H, CH$_3$), 1.69 (m, 2H, CH$_2$), 3.11 (m, 2H, CH$_2$—NC), 3.37 (m, 2H, CH$_2$-NHCO), 4.57 (s, 1 H, NH). $^{13}$C NMR (62 MHz, CDCl$_3$): 26.5 (CH$_2$), 26.6 (CH$_2$), 28.5 (CH$_3$), 28.9 (CH$_2$), 29.0 (CH$_2$), 29.1 (CH$_2$), 29.9 (CH$_2$), 40.5 (CH$_2$—NC), 41.5 (CH$_2$—NH), 77.4 (C), 156.6 (CO), 155.9 (NC).
1-(4-methoxybenzyloxycarbonyl)-N'-2-formylethylenediamine:

Synthesis of N-(4-methoxybenzyloxycarbonyl)-ethylenediamine according to procedure [L. S. Richter, R. N. Zuckermann, *Bioorg. Med. Chem. Lett.*, 5, 1159–1162 (1995)], the organic methylene chloride phase being washed twice with 100 ml of saturated sodium chloride solution each time. Yield: 7.1 g, 64% (lit.: 6.0 g, 54%).

7.1 g of N-(4-methoxybenzyloxycarbonyl)-ethylenediamine are refluxed in 100 ml of ethyl formate and a spatula tip of 4-dimethylaminopyridine for 3 hours. The excess ethyl formate is removed in vacuo using a rotary evaporator. The remaining solid is taken up in 100 ml of CH$_2$Cl$_2$ and is extracted by shaking with 30 ml of H$_2$O. The organic phase is dried with Na$_2$SO$_4$ and concentrated in vacuo using a rotary evaporator. The remaining oil (6.53 g, 81% yield) crystallises after some time and is sufficiently pure for further reaction.

$^1$H NMR (250 MHz, CDCl$_3$): 3.37 (m, 4H), 3.80 (s, 3H), 5.02 (s, 2H), 5.28 (s, br, 1H), 6.32 (s, br, 1H), 6.87 (m, 2H), 7.27 (m, 2H), 8.14 (s, br, 1H). $^{13}$C NMR (62 MHz, CDCl$_3$): 39.0, 40.6, 55.3, 66.8, 113.9, 128.4, 129.9, 159.7, 161.8, 163.4.

R$_f$ (CH$_2$Cl$_2$/MeOH 9/1): 0.6.
N-1-(4-methoxybenzyloxycarbonyl)-2-isocyano-1-aminoethane:

3.97 g of POCl$_3$ (25.91 mmol) are slowly added dropwise within a period of ½ hour to 6.53 g of N1-(4-methoxybenzyloxycarbonyl)-N'-2-formylethylenediamine (25.9 mmol) and 10.85 ml of triethylamine (78 mmol) in 100 ml of CH$_2$Cl$_2$, the temperature being regulated with an ice bath, and the mixture is stirred at 0° C. for a further 4 hours. An aqueous solution of 5.51 g of Na$_2$CO$_3$ in 40 ml of H$_2$O is slowly added dropwise at 0° C. Finally, the mixture is stirred for a further 1 hour at room temperature. The mixture is diluted with a further 100 ml of water, the organic phase is separated off and the aqueous phase is extracted twice with 50 ml of CH$_2$Cl$_2$ each time. The combined organic phases are dried with MgSO$_4$ and concentrated in vacuo using a rotary evaporator. 6.0 g (99%) of a red solid remain, the purity of which is sufficient for the subsequent reactions. An analytical sample, recrystallised from ethyl acetate, yields a colourless solid.

$^1$H NMR (250 MHz, CDCl$_3$): 3.43 (m, 2H), 3.53 (m, 2H), 3.80 (s, 3H), 5.04 (s, 2H), 5.50 (s, br, 1H), 6.88 (m, 2H), 7.28 (m, 2H). $^{13}$C NMR (62 MHz, CDCl$_3$): 40.2, 41.8, 55.3, 66.9, 114.0, 128.2, 130.0, 156.4, 159.7. R$_f$ (CH$_2$Cl$_2$/MeOH 9/1): 0.8.

Example 1

1 mmol of thymineacetic acid, 1 mmol of oxo component, 1 mmol of amine component and 1 mmol of isocyanide component are stirred in 1 ml of methanol for 24 hours and the product that precipitates out is filtered off. The yields can be increased by concentrating the filtrate to half and filtering it again.

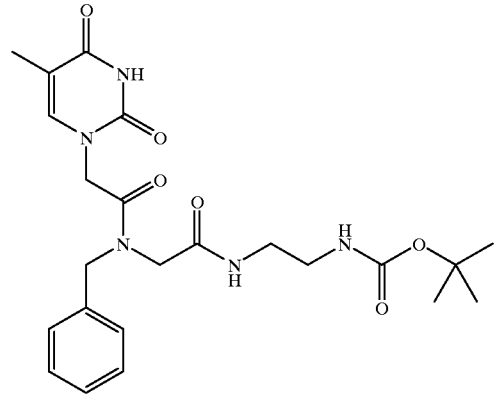

C$_{23}$H$_{31}$N$_5$O$_6$; M$_W$: 473.53342; $^1$H NMR (360 MHz/d$_6$-DMSO): 1.35 (9H, s), 1.76 (3H, s), 2.95–3.1 (4H, m), 3.77 and 3.93 (2H, 2×s {rotamers}), 4.46, 4.58, 4.62, 4.67, 4.76, 4.80 (4H, 6×s {rotamers}), 6.78 (1H, m), 7.21–7.39 (6H, m), 7.87 and 8.13 (1H, 2×tr {rotamers}), 11.29 (1H, s, thymine-NH). $^{13}$C NMR (62.9 MHz): 11.7, 28.1, 47.9, 48.8, 49.5, 77.5, 107.9, 127.1, 127.4, 127.6, 128.2, 128.5, 136.1, 136.8, 142.2, 150.9, 155.5, 158.0, 164.3, 167.2. ES-MS: 474.0 (m+H)$^+$.

Example 2

1 mmol of thymineacetic acid, 1 mmol of oxo component, 1 mmol of amine component and 1 mmol of isocyanide component are stirred in 1 ml of methanol for 24 hours and the product that precipitates out is filtered off. The yields can be increased by concentrating the filtrate to half and filtering it again.

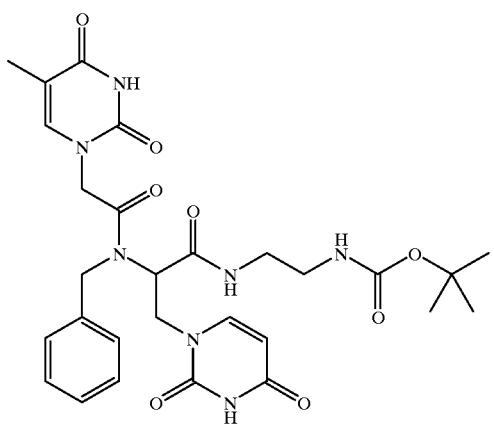

Example 3

1 mmol of thymineacetic acid, 1 mmol of oxo component, 1 mmol of amine component and 1 mmol of isocyanide component are stirred in 1 ml of methanol for 24 hours and the product that precipitates out is filtered off. The yields can be increased by conncentrating the filtrate to half and filtering it again.

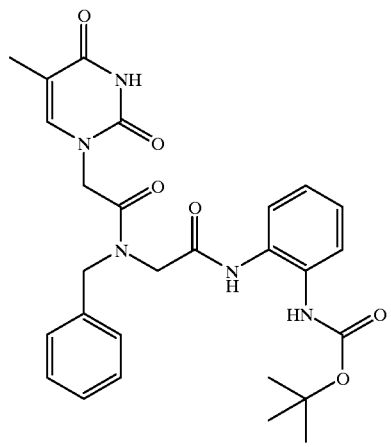

Example 4

1 mmol of thymineacetic acid, 1 mmol of oxo component, 1 mmol of amine component and 1 mmol of isocyanide component are stirred in 1 ml of methanol for 24 hours, and the product that precipitates out is filtered off. The yields can be increased by concentrating the filtrate to half and filtering it again.

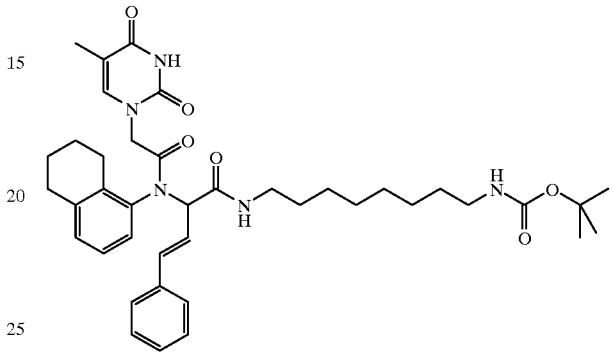

Example 5

Thymine-1-acetic acid in methanol and 1-isocyano-2-N-tert-butoxycarbonylethane in methanol are introduced into each well of a deep-well multi-titre plate made of polypropylene with each well having a volume of 1 ml. The amines shown below are added to rows A–H and the oxo components shown below are added to columns 1–12. The sealed MTPs are shaken at room temperature and the products that precipitate out are filtered off. In order to increase the yields, the filtrate can be concentrated to half and the products that precipitate out again are filtered off. The products are characterised by HPLC-ES, TLC and by $^1H/^{13}C$ NMR.

Components introduced into the 96 MTP:

| Rows containing amine components: | Columns containing oxo components: |
|---|---|
| A 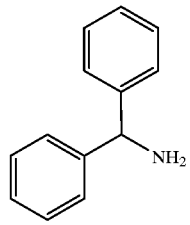 | 1 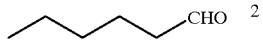 2 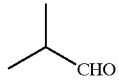 |

-continued

Components introduced into the 96 MTP:

| Rows containing amine components: | | Columns containing oxo components: | |
|---|---|---|---|
| B | MeO-CH₂CH₂-NH₂ | 3 PhCH₂CH₂CHO | 4 p-tolyl-CHO |
| C | 4-fluoroaniline | 5 cinnamaldehyde | 6 furfural |
| D | α-methylbenzylamine | | |
| E | benzylamine | 7 cyclohexanone | 8 1-benzyl-4-piperidinone |
| F | cyclohexylamine | | |
| G | 3-morpholinopropylamine | 9 indanone | 10 glycoside-furan-CHO |
| H | 3-pyridylmethylamine | 11 salicylaldehyde | 12 acetone | e.g. well H10 contains the following compound

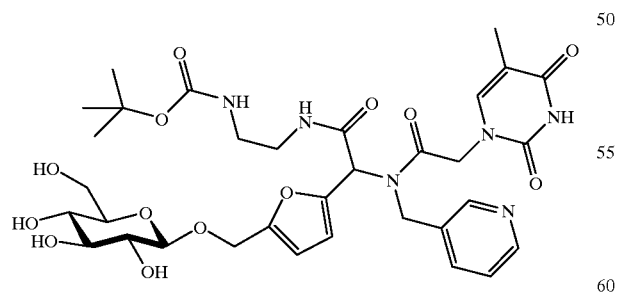

Example 6

Preparation of a thymine pentamer:

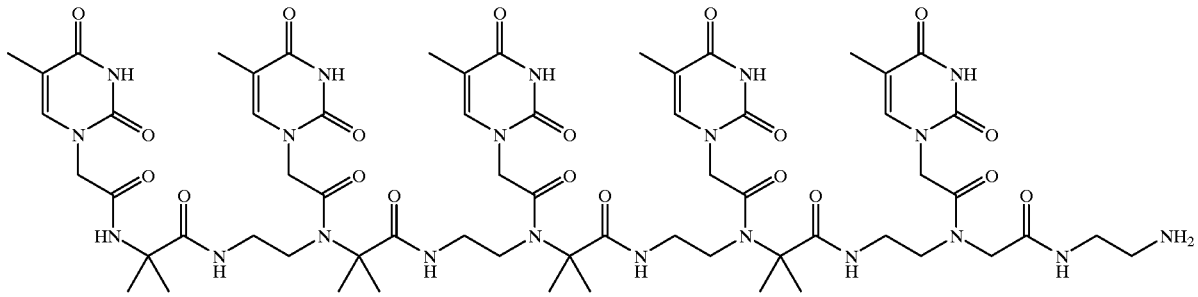

$C_{65}H_{93}N_{21}O_{20}$; $M_W$=1488.56; HPLC-ESI-MS: corresponds;

To prepare that compound on Fmoc-Rink amide resin, the following synthesis scheme is used:
1. Remove the Fmoc group of the Rink resin with morpholine.
2. Shake the so treated resin with acetone, thymineacetic acid and N-1-(4-methoxybenzyloxycarbonyl)-2-isocyano-1-aminoethane in DMSO/DMF.
3. Capping step with acetic anhydride in DMF.
4. Remove the Moz protecting group with 5% trifluoroacetic acid, 2.5% thioanisole, 2.5% dimercaptoethane in $CH_2Cl_2$.
5. Neutralise with morpholine.
6. Repeat steps 2–5 four times.
7. Remove from the resin with 95% TFA.

Example 7

1 mmol of thymineacetic acid, 1 mmol of oxo component, 1 mmol of amine component and 1 mmol of isocyanide component are stirred in 1 ml of methanol for 24 hours and the product that precipitates out is filtered off. The yields can be increased by concentrating the filtrate to half and filtering it again.

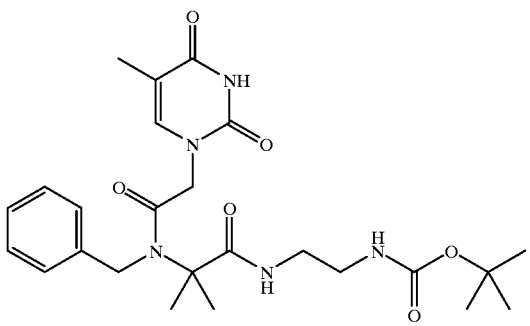

$^1$H NMR (250 MHz/$d_6$-DMSO): 1.23 (6H, s), 1.37 (9H, s), 1.75 (3H, s), 2.95–3.17 (4H, m), 4.58 (2H, s), 4.73 (2H, s), 6.70 (1H, tr), 7.29–7.50 (6H, m), 11.25 (1H, d, thymine-NH). $^{13}$C NMR (62.9 MHz): 12.2, 24.4, 28.5, 43.0, 47.4, 49.7, 62.9, 78.0, 108.0, 126.9, 127.5, 128.9, 128.2, 138.8, 142.6, 151.4, 156.1, 164.8, 169.9, 174.1. ES-MS: 502.0 (m+H)$^+$.

Example 8

1 mmol of thymineacetic acid, 1 mmol of oxo component, 1 mmol of amine component and 1 mmol of isocyanide component are stirred in 1 ml of methanol for 24 hours and the product that precipitates out is filtered off. The yields can be increased by concentrating the filtrate to half and filtering it again.

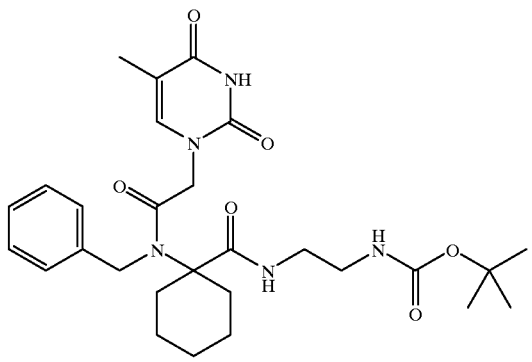

$^1$H NMR (360 MHz/$d_6$-DMSO): 0.83–1.54 (8H, m), 1.37 (9H, s), 1.75 (3H, s), 2.24 (2H, m), 2.95–3.17 (4H, m), 4.56 (2H, s), 4.73 (2H, s), 6.67 (1H, tr), 7.27–7.48 (6H, m), 11.28 (1H, s, thymine-NH). $^{13}$C NMR (62.9 MHz): 11.6, 22.0, 24.7, 28.0, 32.2, 46.6, 49.7, 65.2, 77.4, 107.8, 126.5, 126.9, 128.4, 138.1, 136.1, 142.1, 142.4, 151.0, 155.5, 157.1, 164.3, 167.7, 172.7. ES-MS: 542.0 (m+H)$^+$.

Example 9

1 mmol of thymineacetic acid, 1 mmol of oxo component, 1 mmol of amine component and 1 mmol of isocyanide component are stirred in 1 ml of methanol for 24 hours and the product that precipitates out is filtered off. The yields can be increased by concentrating the filtrate to half and filtering it again.

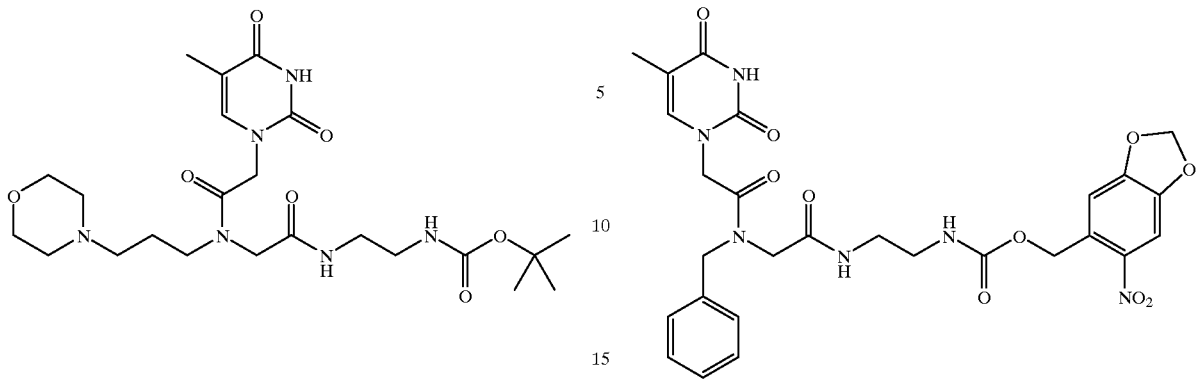

$C_{23}H_{48}N_6O_7$; $M_W$: 520.67501; $^1$H NMR (250 MHz/d$_6$-DMSO):. $^{13}$C NMR (62.9 M Hz): 11.8, 23.7, 24.0, 28.1, 44.9, 45.6, 47.9, 49.8, 53.0, 54.4, 55.3, 66.1, 77.6, 107.8, 142.3, 150.9, 155.5, 164.3, 166.9, 167.3, 167.9, 168.0. ES-MS: 522 (m+H)$^+$.

Example 10

Procedure analogous to the preceding Examples.

Isocyanide component: 1-isocyano-3-N-(tert-butoxycarbonyl)propane.
Oxo component: paraformaldehyde.
Amine component: benzylamine
Acid component: N-(p-methoxybenzoyl)-N$_9$-adenineacetic acid.
$C_{32}H_{38}N_8O_6$; $M_W$=630.71; ES-MS: 632 (m+H)$^+$.

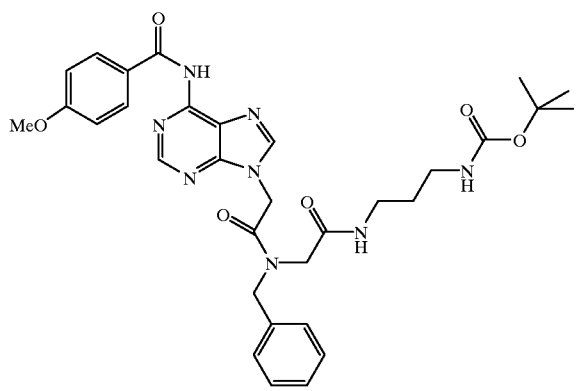

Example 11

1 mmol of thymineacetic acid, 1 mmol of oxo component, 1 mmol of amine component and 1 mmol of isocyanide component are stirred in 1 ml of methanol for 24 hours and the product that precipitates out is filtered off. The yields can be increased by concentrating the filtrate to half and filtering it again.

$C_{27}H_{28}N_6O_{10}$; $M_W$=596.56;

What is claimed is:

1. A process for the preparation of compounds of formula (I)

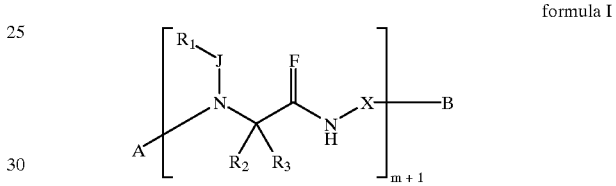

formula I wherein compounds of formulae

A—NH$_2$  II

R$_1$—G  III

R$_2$—C(O)—R$_3$ and  IV

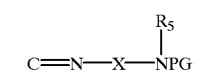

V are reacted with one another, optionally simultaneously, in a first step,
optionally one or more protecting groups are removed,
and the reaction is repeated m times,
wherein, after the first step, the product of each preceding step is used instead of the compound of formula II,
wherein m is 0 or an integer from 1 to 1000,
A is a radical of the amine component being a radical customary in the Ugi reaction,
B is a hydrogen atom, a substituent, (cyclo)alkyl, (cyclo)alkenyl, (cyclo)alkynyl, aroyl, heteroaroyl, a heterocycle, a fluorescent label, an intercalator, an antibiotic, a minor groove binder, a major groove binder, a biotinyl radical, an intercalating radical, an alkylating radical, a steroid, a lipid, a polyamine, an agent that facilitates cell uptake, a saccharide or oligosaccharide, an antisense polymer, a peptide, an antibody conjugate, a polymer or a modified surface or a radical X--NPG of compound V, $R_1$-G is selected from structures of the following formulae:

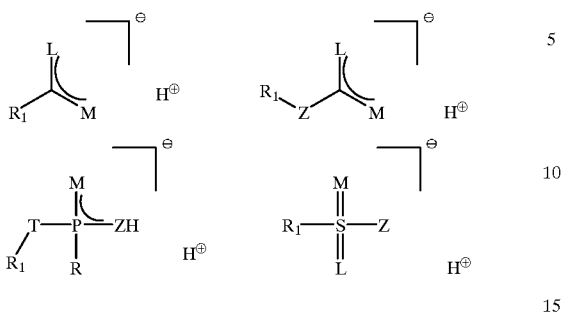

wherein the group $R_1$-G can be linked to the compound of formula IV by way of a molecular spacer via $R_1$ or R or $R_4$;

$R_1$ and R each independently of the other is a radical of the acid component being a radical customary in the Ugi reaction;

L, M, T and Z each independently of the others represents O, S or $NR_4$, wherein $R_4$ represents H, fluorine, (cyclo)alkyl, (cyclo) alkenyl, (cyclo) alkynyl, aroyl, heteroaroyl, heterocycle or —O(cyclo)alkyl, —Oaroyl, —S(cyclo)alkyl, —Saroyl;

$R_2$ and $R_3$ each independently of the other represents a radical of the oxo component being a radical customary in the Ugi reaction, X has the following structure:

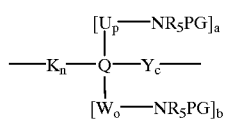

VI each PG independently of any others represents an optionally orthogonal protecting;

each of the radicals Rs independently of any others represents a hydrogen atom, an unsubstituted or substituted alkyl, cycloalkyl, alkoxyalkyl or aryl group or a heterocycle;

the radicals U, W, K and Y each independently of the others represents an unsubstituted or substituted alkyl, alkenyl, alkynyl, alkanoyl, alkoxyalkanoyl, cycloalkyl or aryl group, an unsubstituted or substituted heterocycle or the group $NR_5$, wherein $R_5$ is as defined above;

a, b, c, n, o and p each independently of the others is an integer from 0 to 10;

Q is an unsubstituted or substituted alkyl, aryl, alkenyl, alkynyl, mono- or poly-valent alkanoyl, cycloalkyl, alkoxyalkanoyl, cycloalkanoyl or aroyl group or an unsubstituted or substituted heterocycle, or one of the groups $NR_5$, P, P(O), P(S), B, $BR_5$ and $SO_2$, wherein $R_5$ is as defined above and each of the indices a, b, o and p has a corresponding value;

F is an oxo, thio, seleno or imino group, and

J is selected from the following structures, wherein the upper vertical line represents the bond with $R_1$ and the lower vertical line represents the bond with the nitrogen atom of the main chain of the polymer in the general formula I:

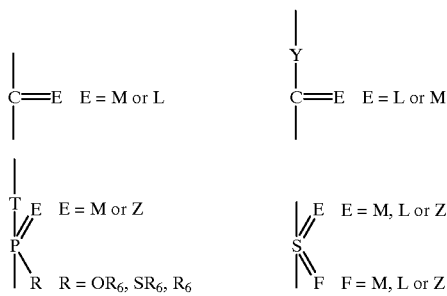

wherein $R_6$ represents H, a substituent, (cyclo)alkyl, (cyclo)alkenyl, (cyclo)alkynyl, aroyl, heteroaroyl or heterocycle, with the proviso that at least one of the radicals R and $R_1$ in the compound of formula I is a radical derived from a natural or synthetic nucleobase.

2. The process according to claim 1, wherein the fluorescent label is fluorescein, Texas red, lissamine rhodamine, cyanine or rhodamine, the intercalators are psoralen, acridine, phenanthroline, a phenanthroline/metal complex or ellipticine, the antibiotics are endiines, β-lactams, tetracyclins, anthracyclins, polyethers, mitomycin antibiotics, phosphomycin antibiotics, macrolides, bleomycin antibiotics or an aminoglycoside, the minor groove binder is netropsin or distamycin, the polyamine is a spermidine polyamine, the antisense polymer is a (5'- or 3'-linked) DNA strand or a (5'- or 3'-linked) RNA strand or a phosphothioate, the peptide is linked at the N- or C-terminal, the antibody conjugate is selected from antibody conjugates that provide cell-specific uptake, are responsive to specific carrier systems or bring about endocytosis, the synthetic polymer is controlled pore glass, a product which is a silica with a pore size of 25–300 nm, a product which is a polystyrene based p-benzloxbenzyl alcohol resin, or a product which consists of about 30% of a porous matrix of approx. 1% cross-linked polystyrene on to which 70% PEG with an average molecular weight of 3000 g/mol has been grafted by oligomerization of oxirane, the natural nucleobases are adenine, thymine, guanine, cytosine or uracil and the synthetic nucleobases are pseudouracil, 5-propynyluracil, 5-hexenyluracil, 5-fluorocytidine, 5-hydroxymethyluracil, 5-methylcytidine, 5-bromocytidine and compounds of the following formulae

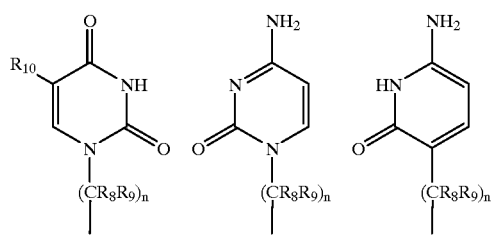

-continued

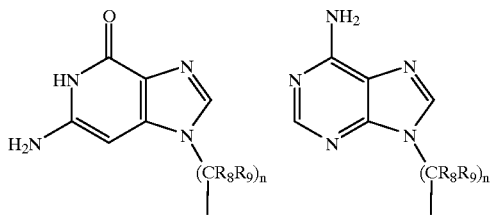

wherein $R_8$ and $R_9$ each independently of the other is H, alkyl, (cyclo)alkenyl, (cyclo)alkynyl, aroyl, heteroaroyl, heterocycle, chlorine or fluorine, $R_{10}$=fluorine, bromine, iodine, chlorine, alkynyl, alkyl, aroyl, heteroaroyl or H, and n=from 1 to 20 and wherein the side groups of the bases may have protecting groups.

3. The process according to claim 1, wherein m=from 1 to 200.

4. The process according to claim 1, wherein in each reaction step at least one of the components III, IV and V is varied.

5. The process according to claim 1, wherein the process is carried out on a solid phase.

6. A compound of formula V

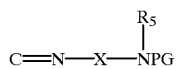

wherein X has the following structure:

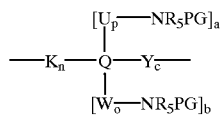

and each PG independently of any others is an optionally orthogonal protecting group;
each of the radicals $R_5$ independently of any others represents a hydrogen atom, an unsubstituted or substituted alkyl, cycloalkyl, alkoxyalkyl or aryl group or a heterocycle;
the radicals U, W, K and Y each independently of the others represents an unsubstituted or substituted alkyl, alkenyl, alkynyl, alkanoyl, alkoxyalkanoyl, cycloalkyl or aryl group, an unsubstituted or substituted heterocycle or the group $NR_5$, wherein $R_5$ is as defined above;
a, b, c, n, o and p each independently of the others is an integer from 0 to 50;
Q is an unsubstituted or substituted alkyl, aryl, alkenyl, alkynyl, mono- or poly-valent alkanoyl, cycloalkyl, alkoxyalkanoyl, cycloalkanoyl or aroyl group or an unsubstituted or substituted heterocycle, or one of the groups $NR_5$, P, P(O), P(S), B, $BR_5$ and $SO_2$, wherein $R_5$ is as defined above and each of the indices a, b, o and p has a corresponding value.

7. The compound according to claim 6, wherein
the radicals PG represent N-acyl derivatives or N-alkyl derivatives;
each of the radicals $R_5$ independently of any others represents a hydrogen atom or an unsubstituted or substituted alkyl or aryl group;
the radicals U, W, K and Y each independently of the others represents an unsubstituted or substituted alkyl, cycloalkyl or aryl group;
a, b, c, n, o and p each independently of the others is an integer from 0 to 5;
Q represents at least an unsubstituted alkyl, aroyl or aryl group or an unsubstituted or substituted heterocycle.

8. A process for the preparation of a compound of formula V, wherein a compound of formula VII

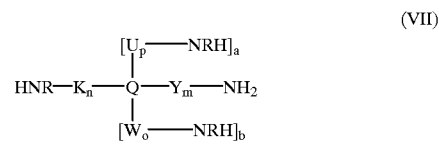

is protected with the above-defined groups PG, which may be independent of one another resulting in a compound of formula VIII

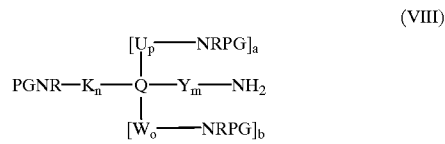

and then the compound of formula VIII is reacted to form an isonitrile of formula V.

9. The process according to claim 8, wherein the compound of formula VIII is reacted with formulation reagents to form a compound of formula IX:

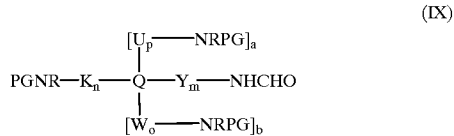

which is then reacted to form a compound of formula V, the radicals and indices being as defined in claim 1.

10. A process for the preparation of a compound of formula IX,
wherein, starting from a compound of formula (X)

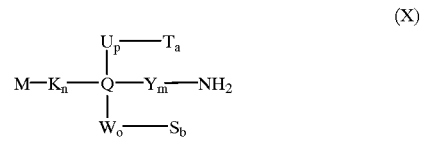

wherein the radicals and indices are as defined in claim 1, first the amine function is formulated, then one or more of the functionalities M, T and S, which each independently of the others represents a halogen or a hydroxy function, is/are converted into one or more azide functions, those azides are converted into the corresponding amines and the amines are then reacted with the protecting groups as defined in claim 1.

* * * * *